United States Patent
Schweizer et al.

(10) Patent No.: US 7,777,189 B2
(45) Date of Patent: Aug. 17, 2010

(54) DIRTY ISOTOPE PET RECONSTRUCTION

(75) Inventors: Bernd Schweizer, Herzogenrath (DE); Heinrich von Busch, Aachen (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 210 days.

(21) Appl. No.: 12/293,089

(22) PCT Filed: Mar. 8, 2007

(86) PCT No.: PCT/US2007/063561

§ 371 (c)(1), (2), (4) Date: Sep. 16, 2008

(87) PCT Pub. No.: WO2007/117801

PCT Pub. Date: Oct. 18, 2007

(65) Prior Publication Data

US 2009/0057561 A1 Mar. 5, 2009

Related U.S. Application Data

(60) Provisional application No. 60/767,413, filed on Mar. 27, 2006.

(51) Int. Cl.
*G01T 1/166* (2006.01)
(52) U.S. Cl. .................................. 250/363.04
(58) Field of Classification Search .............. 250/252.1, 250/363.02, 363.03, 363.04, 363.07, 363.09
See application file for complete search history.

(56) References Cited

U.S. PATENT DOCUMENTS

| | | | |
|---|---|---|---|
| 6,008,493 A | 12/1999 | Shao et al. | |
| 6,198,104 B1 | 3/2001 | Geagan et al. | |
| 6,631,284 B2 * | 10/2003 | Nutt et al. | 600/427 |
| 2004/0030246 A1 * | 2/2004 | Townsend et al. | 600/427 |
| 2004/0195512 A1 * | 10/2004 | Crosetto | 250/363.04 |
| 2006/0151705 A1 * | 7/2006 | Manjeshwar et al. | 250/363.03 |
| 2008/0285828 A1 * | 11/2008 | Gagnon et al. | 382/131 |

OTHER PUBLICATIONS

Accorsi, R., et al.; Implementation of a Single Scatter Simulation Algorithm for 3D PET: Application to Emission and Transmission Scanning; 2002; Proc. of IEEE Nuclear Science Symposium and Medical Imaging Conference; 5 pgs.

Kull, T., et al.; Quantitative Imaging of Yttrium-86 PET with the ECAT EXACT HR+ in 2D Mode; 2004; Cancer Biotherapy & Radiopharmaceuticals; 19(4)482-490.

Werling, A., et al.; Fast Implementation of the Single Scatter Simulation Algorithm and its use in Iterative Image Reconstruction of PET data; 2002; Phys. Med. Biol.; 47:2947-2960.

* cited by examiner

Primary Examiner—David P Porta
Assistant Examiner—Marcus H Taningco

(57) ABSTRACT

A method for use in dirty isotope positron imaging uses information about a measured characteristic of an object (118) to generate a spurious coincidence correction. The spurious imaging correction is applied to data from a positron imaging examination of the object. The corrected data is used to generate a human readable image indicative of the object.

40 Claims, 10 Drawing Sheets

DIRTY ISOTOPE PET RECONSTRUCTION

CROSS REFERENCE TO RELATED APPLICATIONS

This application claims the benefit of U.S. provisional application Ser. No. 60/767,413 filed Mar. 27, 2006, which is incorporated herein by reference.

The present invention relates to the field of positron emission tomography, and especially to the correction of spurious coincidences resulting from the use of dirty isotopes. It finds particular application to medical imaging and other applications in which it is desirable to reduce the effects of spurious coincidences.

Positron emission tomography (PET) is a branch of nuclear medicine in which a positron-emitting radiopharmaceutical is introduced into the body of a patient or other object under examination. Conventional PET isotopes decay solely by positron emission. The positrons react with an electron in what is known as a positron annihilation event, thereby generating a coincident pair of 511 keV gamma rays which travel in opposite directions along a line of response (LOR). A gamma ray pair detected within a coincidence time is ordinarily recorded by the PET scanner as an annihilation event.

In practice, however, Compton scattering can affect one or both of the 511 keV photons. Such scattering can cause coincidence events to be misplaced inside the object under examination, or even outside the scattering medium, resulting in a degradation of image quality. Accordingly, a single scatter simulation (SSS) technique has been used to correct for Compton scattering of the 511 keV coincident pairs resulting from the decay of conventional radioisotopes. See Accorsi et al., *Implementation of a Single Scatter Simulation Algorithm for 3D PET: Application to Emission and Transmission Scanning*, Proceedings of IEEE Nuclear Science Symposium and Medical Imaging Conference (2002).

Corrected projection data has been generated according to the relationship:

$$P_{corrected} = P_{measured} - a \times S_{Compton} - b \times CF \qquad \text{Equation 1}$$

where $P_{corrected}$ is the corrected projection data, $P_{measured}$ is the measured projection data, $S_{Compton}$ is a Compton scatter estimate obtained using the SSS technique, and CF is a constant or uniform correction factor used to account for errors such as randoms. Scaling factors a and b have been obtained using a best fit algorithm. The corrected data $P_{corrected}$ has been used to reconstruct an image indicative of the radionuclide distribution in the object under examination.

Recent trends have seen a rapid increase in the application range of PET techniques, particularly in medical applications. In many cases, the development of new PET tracers is driven by bio-chemical requirements and the desire to use tracers known from single-photon emission computed tomography (SPECT) or otherwise having relatively well-characterized chemistries. As a result, so-called dirty isotopes such as $^{76}$Br, $^{86}$Y, $^{89}$Zr, $^{94m}$Tc, $^{124}$I, and $^{66}$Ga have begun to garner attention. In contrast to conventional PET isotopes, dirty isotopes decay by positron emission and electron capture alternatively, resulting in the generation of 511 keV annihilation photons from positron emission events, photons at various energies from electron capture events, and so-called prompt photons at various energies in cascade with annihilation photons from positron emission events. Iodine-124, for example, produces 511 keV annihilation photons and moreover 603 keV single photons (both from separate nuclear decays and from a single nuclear decay cascade).

Unfortunately, dirty isotopes can be more difficult to image than conventional isotopes. Their generally lower positron abundance generally results in a reduced number of counts. Moreover, the single photons can lead to spurious coincidences in which the singles are temporally coincident not only with each other, but with 511 keV photons resulting from positron annihilations. Such spurious coincidences create false LORs, thereby degrading the quality of the resultant image.

One technique for reducing the effect of the prompt photons, and hence the spurious coincidences, is to discriminate based on the energy of the detected photons. Depending on the emission spectra of a particular isotope and the energy resolution of a particular scanner, however it may be difficult to distinguish between the prompt and 511 keV photons.

Spurious coincidences have also been accounted for in the second order of a series expansion, where the zeroth and first orders provide corrections for uniform and linear background contributions, respectively. See Kull, et al., *Quantitative Imaging of Yttrium-86 PET With the ECAT EXACT HR+ in 2D Mode*, Cancer Biotherapy and Radiopharmaceuticals, Volume 19, Number 4, 2004. However, the Kull technique assumes that the dirty isotope background distribution is a second order or $n^2$ function. It also does not account for patient or object specific variations which can affect the spurious coincidence background.

Accordingly, it is desirable to provide an improved technique for reducing the effects of spurious coincidences in positron imaging data.

Aspects of the present invention address these matters, and others.

According to a first aspect of the present invention, a positron imaging method includes using information indicative of an attenuation distribution of an object to generate a spurious coincidence correction, applying the spurious coincidence correction to data from a positron imaging examination of the object, and generating a human readable image indicative of the corrected data.

According to another aspect of the invention, a positron imaging apparatus includes means for obtaining data indicative of radionucide decays in an object under examination. The decays include positron decays which result in the emission of temporally coincident photon pairs and decays which result in the generation of single photons. The apparatus also includes means for measuring a physical characteristic of the object, means for using the measured physical characteristic correct for single photons and single photons and single photons of the photon pairs which are detected in coincidence, and means for generating a human readable image indicative of the corrected data.

According to another aspect of the present invention, a computer readable storage medium containing instructions which, when executed by a computer, cause the computer to carry out a method which includes obtaining projection data indicative of positron annihilations in an object under examination, obtaining object specific data indicative of a physical characteristic of the object, generating a spurious coincidence correction, using the spurious coincidence correction to correct the projection data, and generating volumetric image data indicative of the corrected projected data. The correction is a function of the object specific data.

According to another aspect, an imaging method includes obtaining data indicative of positron annihilations in an object under examination, applying a spurious coincidence correction to the data so as to reduce an effect of spurious coincidences in the data, and generating a human readable image indicative of the corrected data. The spurious coincidence correction is a function of an object specific physical characteristic.

According to another aspect, a method includes obtaining measured projection data indicative of positron annihilations in an object under examination, using an object specific correction function to correct for Compton scattering and spurious coincidences in the measured projection data, and generating a human readable image indicative of the corrected projection data.

According to another aspect, an apparatus includes a plurality of radiation sensitive detectors disposed about an examination region, coincidence detection means for generating data indicative of temporally coincident photons detected by the radiation sensitive detectors, means for correcting for scattering and spurious coincidences in the data according to an object specific correction function so as to generate corrected data, and means for generating a human readable image indicative of the corrected data.

According to another aspect of the invention, a method of utilizing positron annihilation includes obtaining data indicative of a plurality of positron annihilations in an object under examination and applying spurious coincidence and attenuation corrections to the data so as to generate corrected data. The spurious coincidence correction is proportional to $$\frac{1}{R\sqrt{1-(x/R)^2}}.$$

where x is a distance from a center of the ring of radiation sensitive detectors. The method also includes generating a human readable image indicative of the corrected data.

According to another aspect, a positron imaging apparatus includes a plurality of radiation sensitive detectors disposed about an examination region in an arc having a radius R and coincidence detection means for generating data indicative of temporally coincident photons detected by the radiation sensitive detectors. The data includes spurious coincidences resulting from the decay of a dirty isotope. The apparatus also includes means for applying spurious coincidence and attenuation corrections to the data so as to generate corrected data, and means (129, 128) for generating a human readable image indicative of the corrected data. The spurious coincidence correction is proportional to $$\frac{1}{R\sqrt{1-(x/R)^2}},$$

Those skilled in the art will appreciate still other aspects of the present invention upon reading and understanding the attached figures and description.

The present invention is illustrated by way of example and not limitation in the figures of the accompanying drawings, in which like references indicate similar elements and in which.

Figure 1:
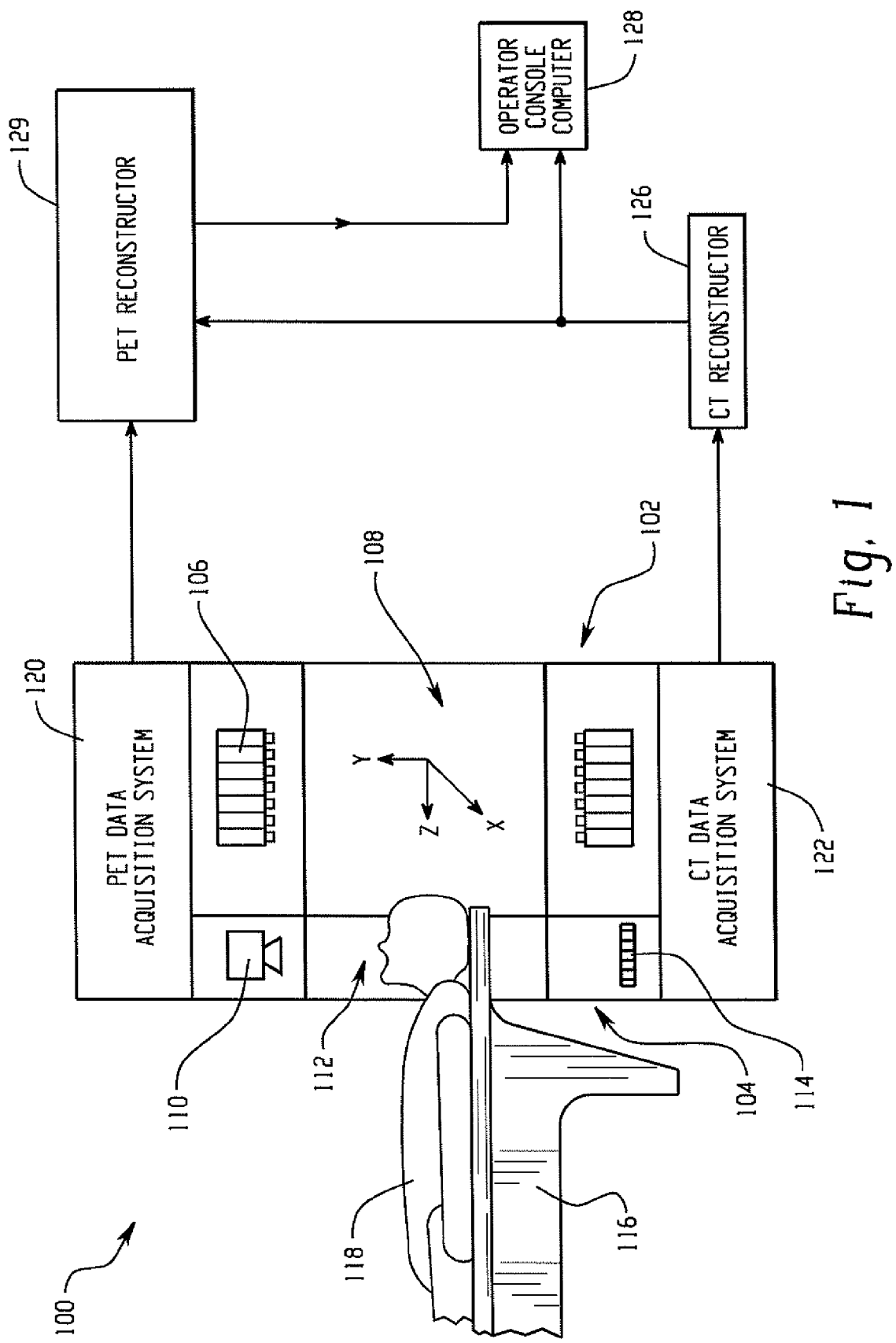
FIG. 1 depicts a combined PET/computed tomography (CT) system.

With reference to FIG. 1, a combined PET/CT system 100 includes a PET gantry portion 102 and a CT gantry portion 104. The PET gantry portion 102 includes one or more axial rings of radiation sensitive detectors 106 which surround an examination region 108. The detectors 106 detect gamma radiation characteristic of positron annihilation events occurring within a PET examination region 108.

The CT portion 104 includes a radiation source 110 such as an x-ray tube which rotates about a CT examination region 112. Radiation sensitive detectors 114 detect radiation emitted by the x-ray source which has traversed the examination region 112.

The PET gantry portion 102 and CT gantry portion 104 are preferably located in proximity with their respective examination regions 108, 112 disposed along a common longitudinal or z-axis. An object support 116 supports an object to be imaged 118 such as human patient. The object support 116 is preferably longitudinally movable in coordination with operation of the PET/CT system 100 so that the object 118 can be scanned at a plurality of longitudinal locations by both the PET and CT gantry portions 102, 104.

In a step and shoot or frame-based mode, the object support 116 is moved to a first longitudinal position. Following the acquisition of the desired data, the support 116 is moved to a second longitudinal position, and the desired data obtained. This process is repeated until the desired longitudinal extent of the object 118 has been scanned. In a continuous mode, the object support 116 is moved substantially continuously during scanning.

A CT data acquisition system 122 processes the signals from the CT detectors 114 to generate data indicative of the radiation attenuation along a plurality of lines or rays through the examination region 112. A CT reconstructor 126 reconstructs the data using suitable reconstruction algorithms to generate volumetric image data indicative of the radiation attenuation of the object 118.

PET data acquisition system 120 generates projection data which includes information indicative of temporally coincident photons and hence positron annihilation events detected by the detectors 106. More particularly, the projection data provides information on the LOR for each event, such as a transverse and longitudinal position of the LOR, its transverse and azimuthal angles, and time of flight (TOF) information in the case of a scanner having TOF capabilities. The data may also be rebinned into one or more sinogram or projection bins. When used to image a dirty isotope, the data may include spurious coincidences resulting from the decay thereof.

A PET reconstructor 129, which preferably includes one or more computer processors, generates volumetric image data indicative of the distribution of the radionuclide in the object 118, typically using an iterative reconstruction algorithm. In addition, the PET reconstructor 129 uses information from the CT system to apply attenuation and other desired corrections to the PET data. Moreover, and as will be described in more detail below, the PET reconstructor 129 also corrects for spurious coincidences in the positron emission data.

Computer readable instructions which cause the reconstructor 129 to carry out the reconstruction and associated corrections are preferably carried on one or more computer readable media such as computer disks, volatile or non-volatile memory, or the like accessible to the processor(s). The instructions may also be transmitted by way of a suitable communications network such as the internet to storage media accessible to the processor(s).

A workstation computer serves an operator console 128. The console 128 includes a human readable output device such as a monitor or display and input devices such as a keyboard and mouse. Software resident on the console 128 allows the operator to view and otherwise manipulate the volumetric image data generated by the PET and CT reconstructors 129, 126. Software resident on the console 128 also allows the operator to control the operation of the system 100 by establishing desired scan protocols, initiating and terminating scans, and otherwise interacting with the scanner 100.

Variations on the system 100 are also contemplated. Thus, for example, the CT portion of the scanner may be omitted, located remotely from the PET gantry portion 102, or replaced with another imaging device such as a magnetic resonance (MR) scanner. Attenuation or anatomical information may also be generated using a transmission source associated with the PET gantry portion 102 or obtained from another source.

Figure 2:
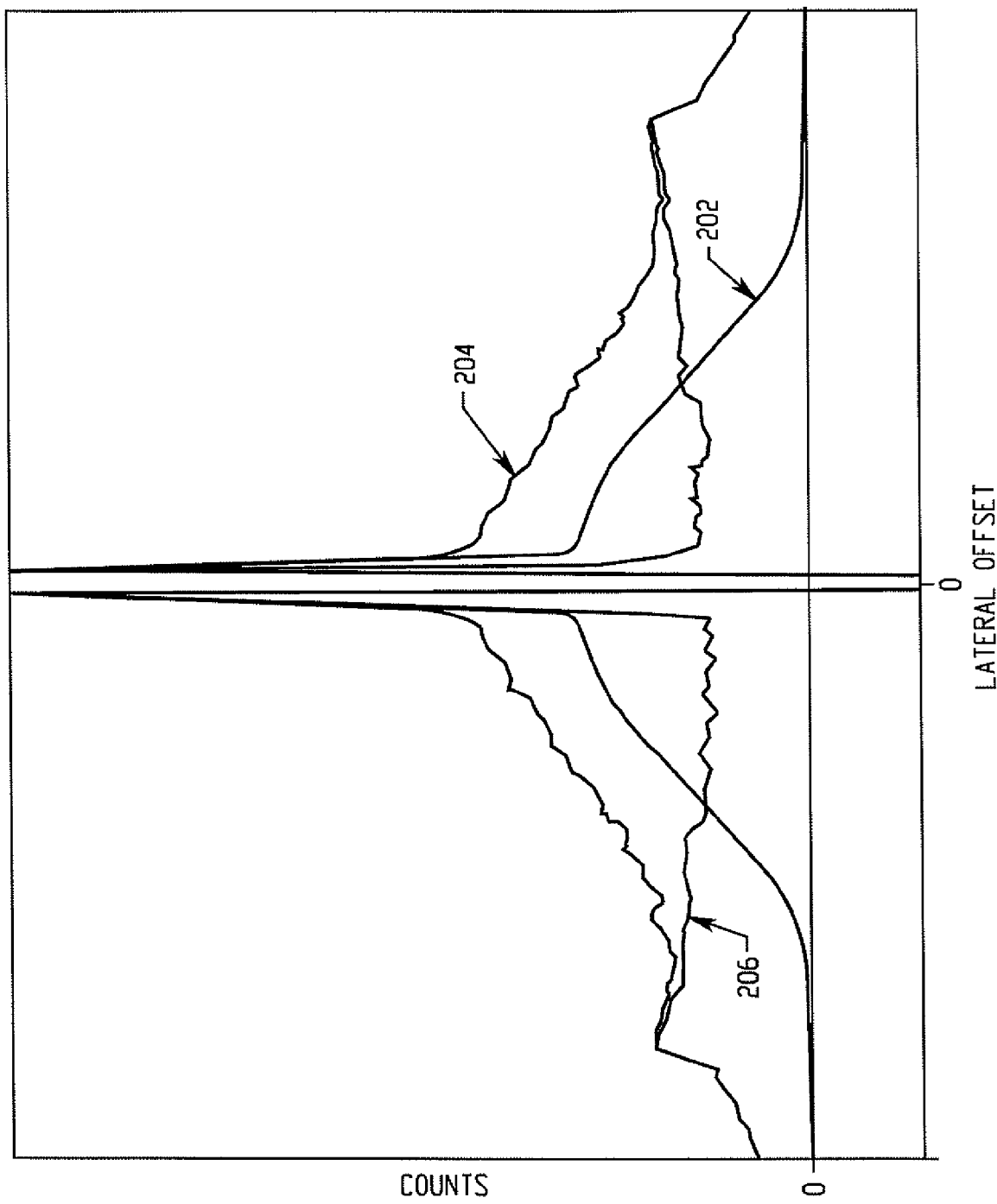
FIG. 2 depicts signal distributions of PET sinograms obtained using a line source embedded in a cylindrical scattering medium.

As discussed above, dirty isotopes are characterized by 511 keV annihilation photons, as well as additional emission lines generated by prompt photons. FIG. 2 depicts the signal distribution of a PET sinogram obtained using a line source embedded in a cylindrical scattering medium and disposed along the z-axis at the center of the PET scanner detector ring 106. The abscissa represents a lateral or radial offset from the center of the detector ring 106 and the ordinate reflects the number of counts.

Distribution 202 shows the distribution obtained using a phantom containing fluorine-18, while distribution 204 shows the distribution obtained using a phantom containing iodine-124. Both distributions were normalized to the same integral in the true counts peak. A third distribution 206 was obtained by subtracting the first, fluorine-18 distribution 202 from the second, iodine-124 distribution 204. The third distribution 206 is indicative of spurious coincidences and is generally bowl shaped, with the spurious coincidences lowest at the center of the detector 106 ring and generally increasing as a non-linear function of the distance therefrom.

Figure 3:
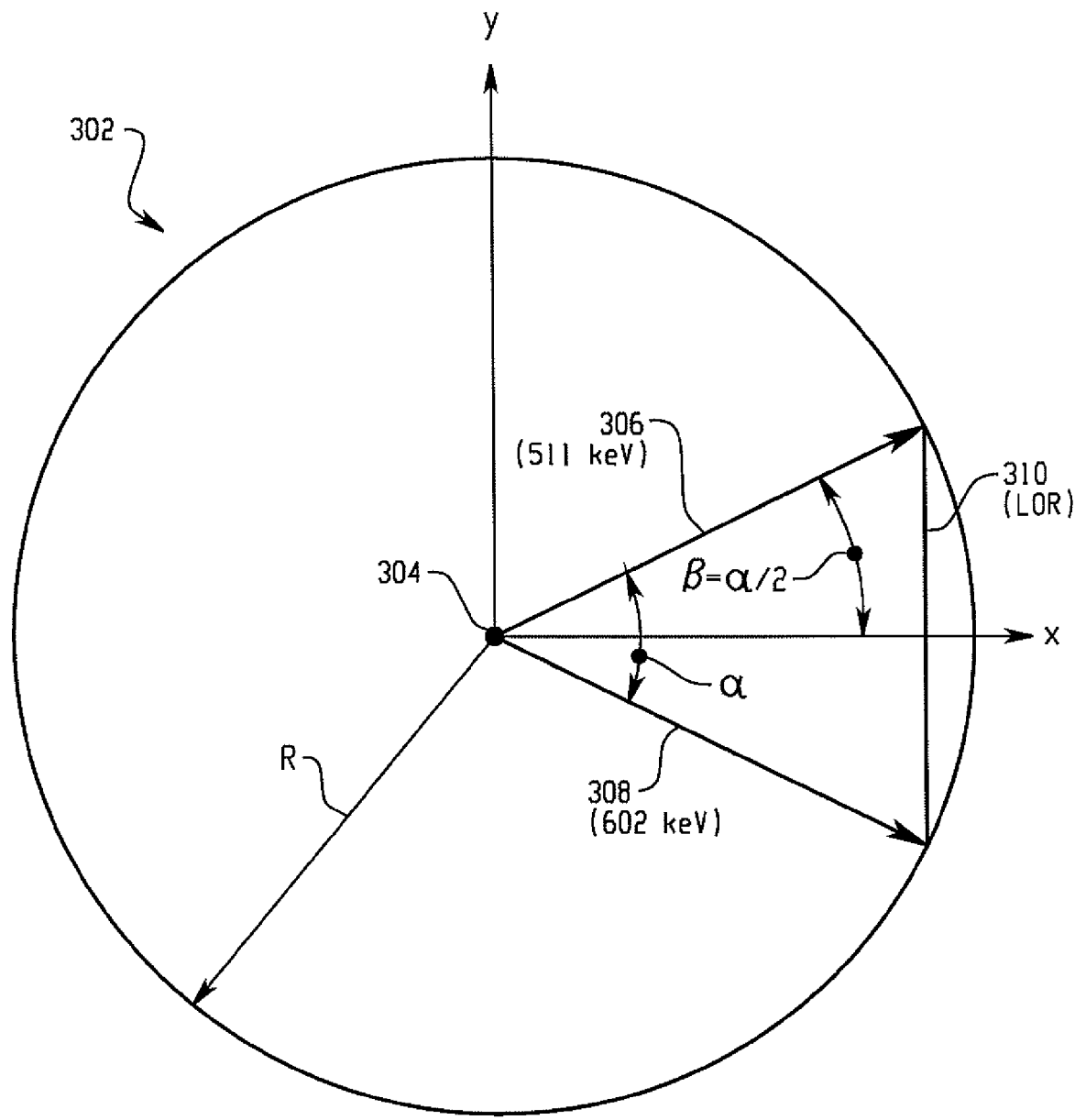
FIG. 3 depicts a two dimensional model of the dirty isotope PET process.

The spurious coincidence distribution may also be derived analytically using a simplified two dimensional model of the dirty isotope PET process. With reference to FIG. 3, the PET scanner detectors 106 are arranged in a circle 302 of radius R. The dirty isotope 304 is modeled as an ideal point source located in the center of the detector ring. In the case of iodine-124, a 511 keV gamma 306 and a 602 keV gamma 308 are modeled as being emitted at random angles α to each other. Their respective intersection points with the detector ring 302 define an additional prompt or spurious coincidence background LOR 310. Note that physical effects such as imperfect detection efficiency, scatter, and attenuation have been omitted from the model.

Photon pairs 306, 308 may be modeled as being emitted symmetrically at angles β=α/2 above and below the x-axis with (0<β<π). The resulting LORs 310 are perpendicular to the x-axis and thus represent a projection of the prompt coincidence background onto the x-axis. Due to the rotational symmetry of the geometry, projections at other angles are identical to the one illustrated in FIG. 3.

The x-coordinate of an LOR 310 may be expressed as:

$$x(\beta) = R \cdot \cos(\beta) \quad \text{Equation 2}$$

Hence:

$$\beta(x) = \arccos\left(\frac{x}{R}\right) \quad \text{Equation 3}$$

The density distributions g(β) and h(x) of LORs 310 expressed as function of β and x are related as follows:

$$g(\beta)d\beta = g(\beta(x)) \cdot \frac{d\beta}{dx} \cdot dx = h(x)dx \quad \text{Equation 4}$$

Because the density distribution g as function of β is a constant (i.e. for each infinitesimal angle step dβ, one further LOR 301 parallel toy is added), it follows from Equation 3 that the LOR 310 density h is proportional to the derivative dβ/dx, with x in the range (−R≦x≦+R):

$$h(x) = \frac{d\beta}{dx} \propto \frac{1}{R\sqrt{1-(x/R)^2}} \quad \text{Equation 5}$$

Note that for the purposes of the present analysis, the proportionality constant is set to 1 to illustrate the shape of the prompt coincidence background.

This is also the required end result for the distribution of prompt coincidence background LORs (due to the detection of only one of the annihilation gammas and the prompt gamma), since the line density for any projection angle is identical to h for symmetry reasons as explained above.

Figure 4:
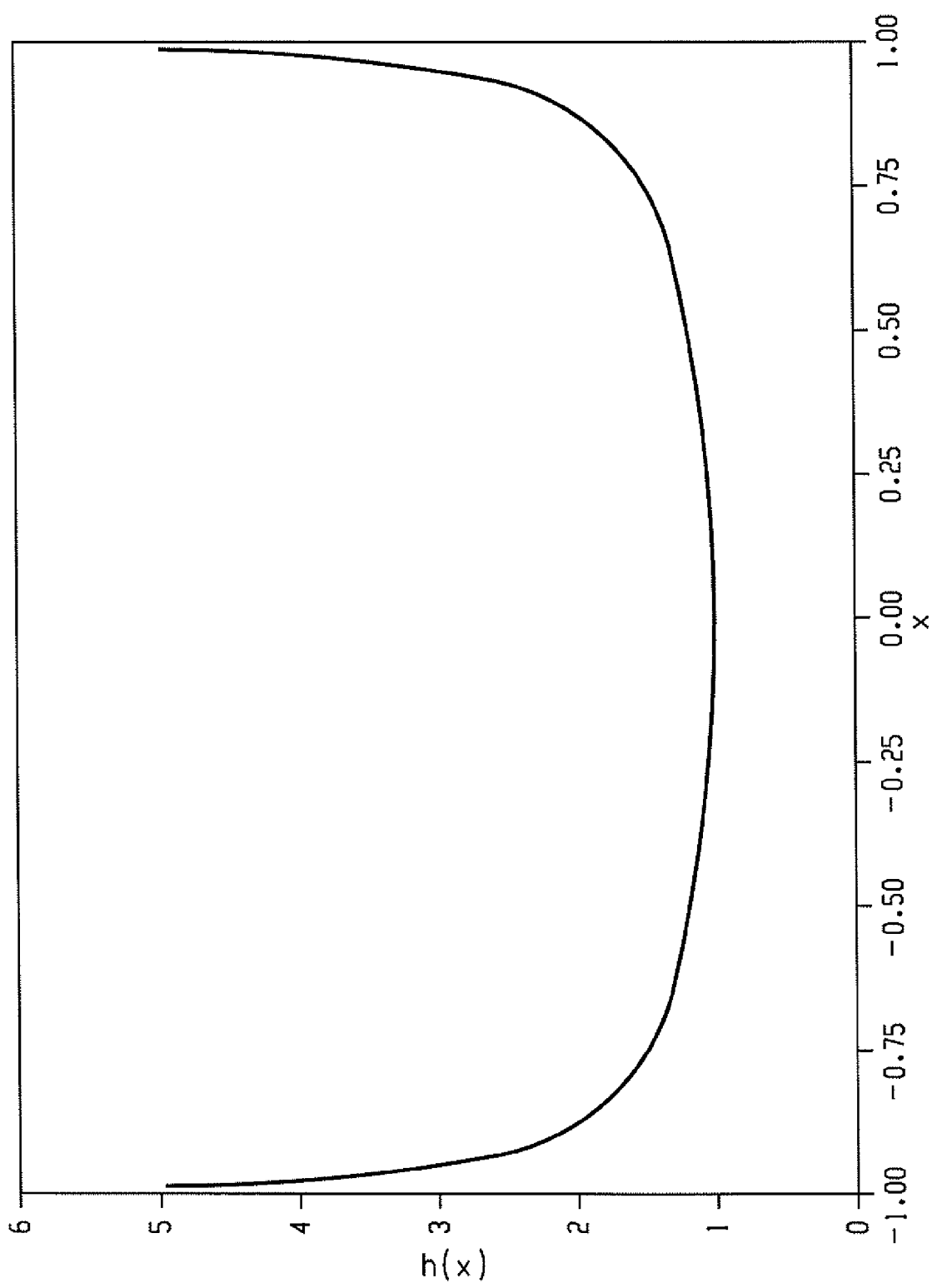
FIG. 4 depicts an analytically derived spurious coincidence distribution.

FIG. 4 shows a plot of the spurious coincidence distribution h(x) for the case R=1 over the entire diameter of the detector ring 302. In real PET scanners, the trans-axial field of view extends only over about half of the ring diameter, corresponding approximately to the range (−0.5<x+0.5) in FIG. 4. Therefore, the singularities present at x=−R and x=+R are not of practical significance.

As will be appreciated, the LOR distribution of Equation 5 was derived for a point source 304 located at the center of the detector ring 302. The derivation may be extended to determine the effect of asymmetrically located sources (i.e., sources which are not centered in the transverse plane).

Figure 5:
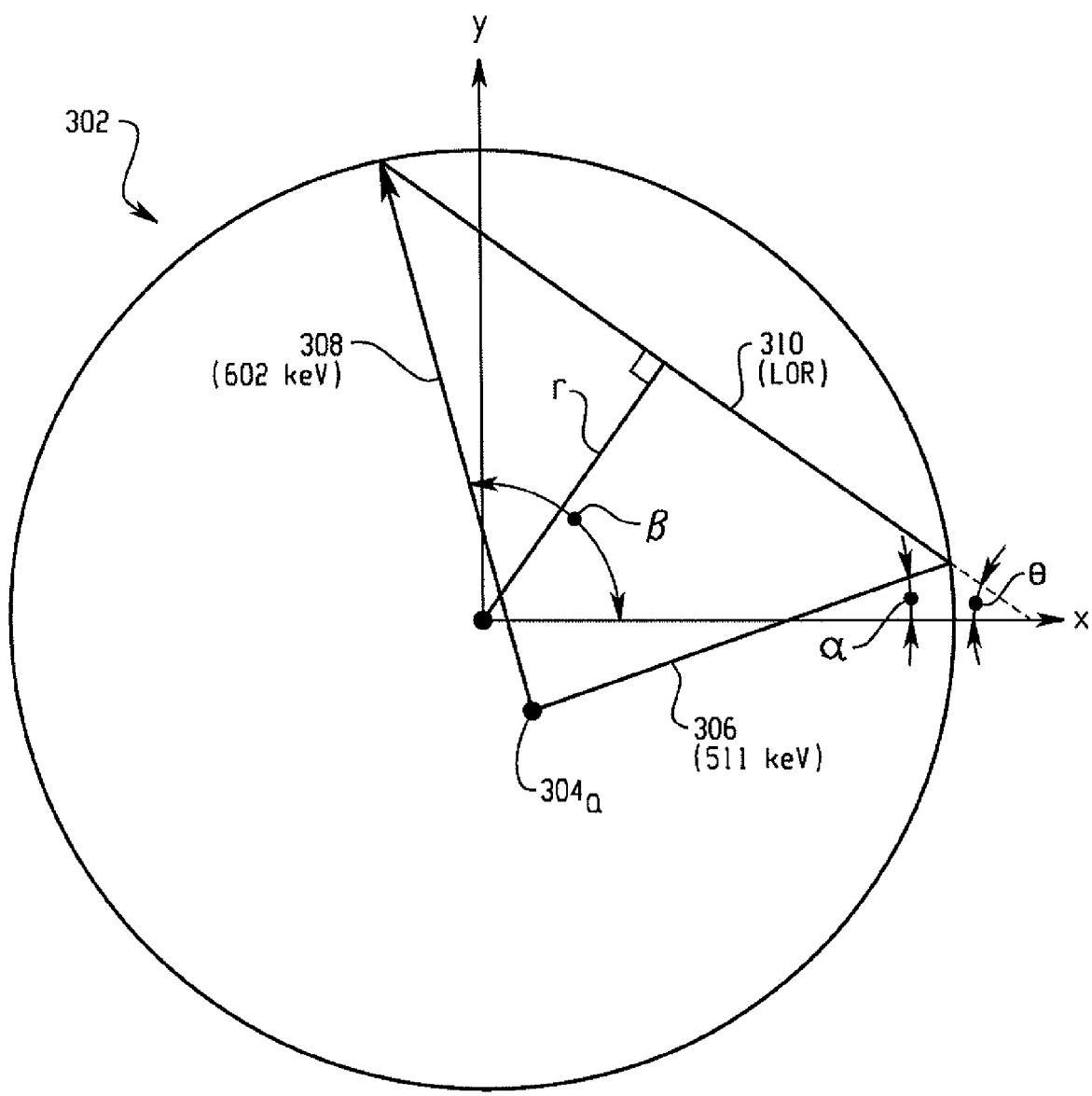
FIG. 5 depicts a two dimensional model of the dirty isotope PET process.

Turning now to the model of FIG. 5, the annihilation photon 306 and the additional prompt gamma 308 can be modeled as being emitted at random angles to each other from an asymmetric source location $304_a$. In a numerical simulation, the emission angle α of the first photon can be incremented in an outer program loop from 0° to 360° in steps of Δα. For each α-value, the direction of the second photon β can then be incremented in an inner loop from 0° to 360° in steps of Δβ. The resulting intersection points with the PET detector circle 302 define a prompt coincidence or spurious LOR 310. The LORs 310 are accumulated into a sinogram according to their distance r from the origin and the angle θ between the LOR 310 and the x-axis. The sinograms can then be summed over all angles to show the line density profile as a function of the distance from the center of the transverse plane.

Figure 6:
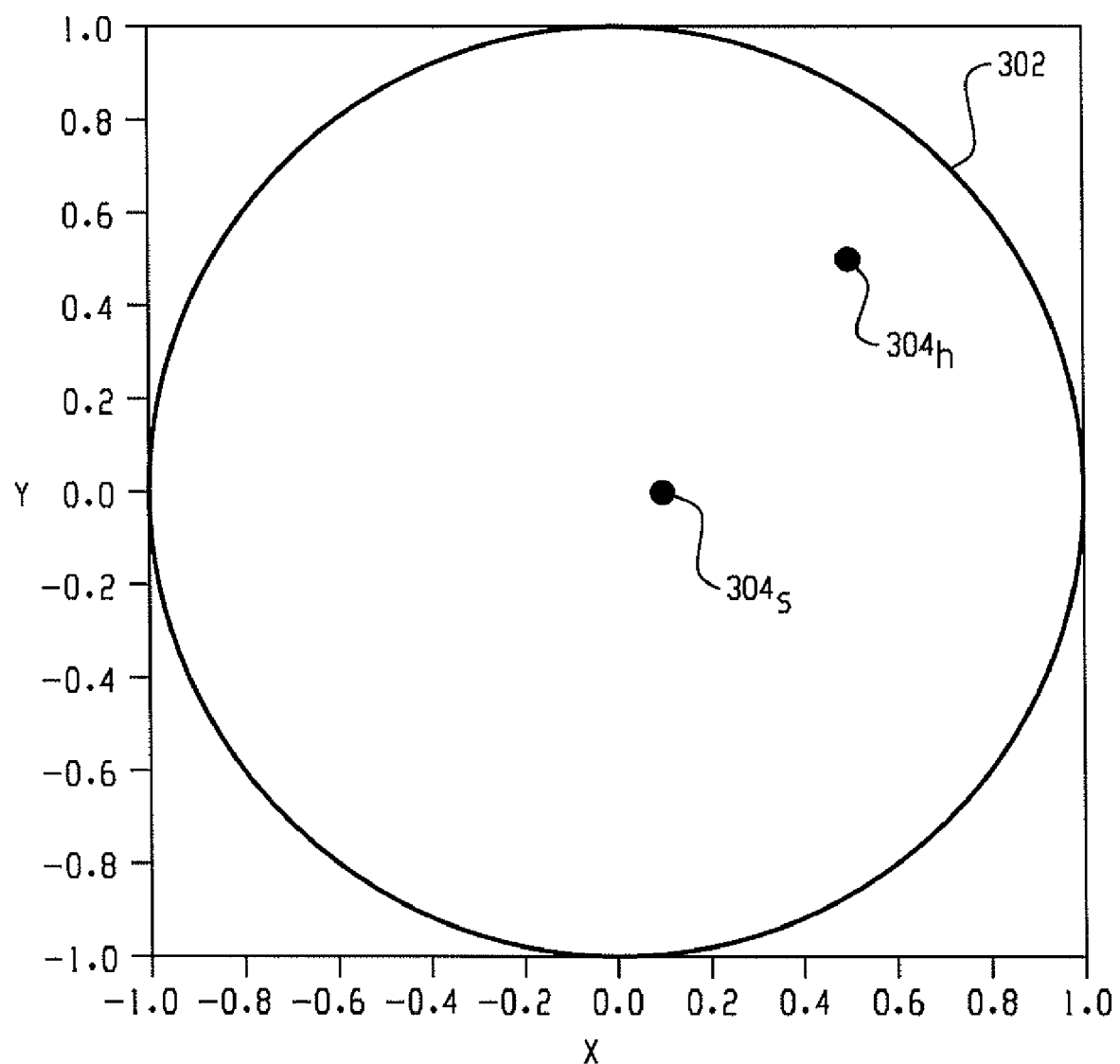
FIG. 6 depicts asymmetric spurious coincidence source locations in relation to the transverse plane.
Figure 7:
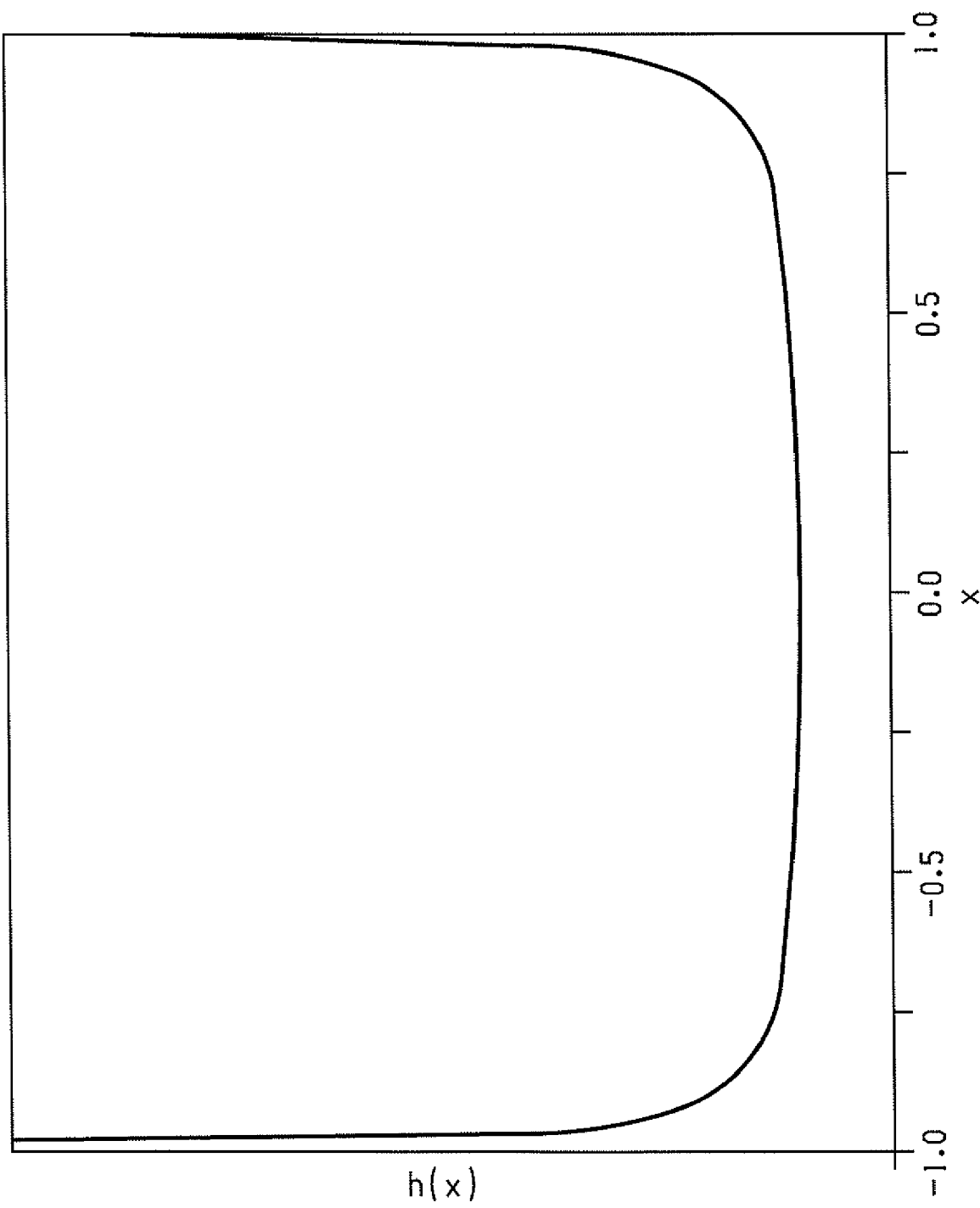
FIG. 7 depicts a spurious coincidence distribution for a slightly asymmetric source.
Figure 8:
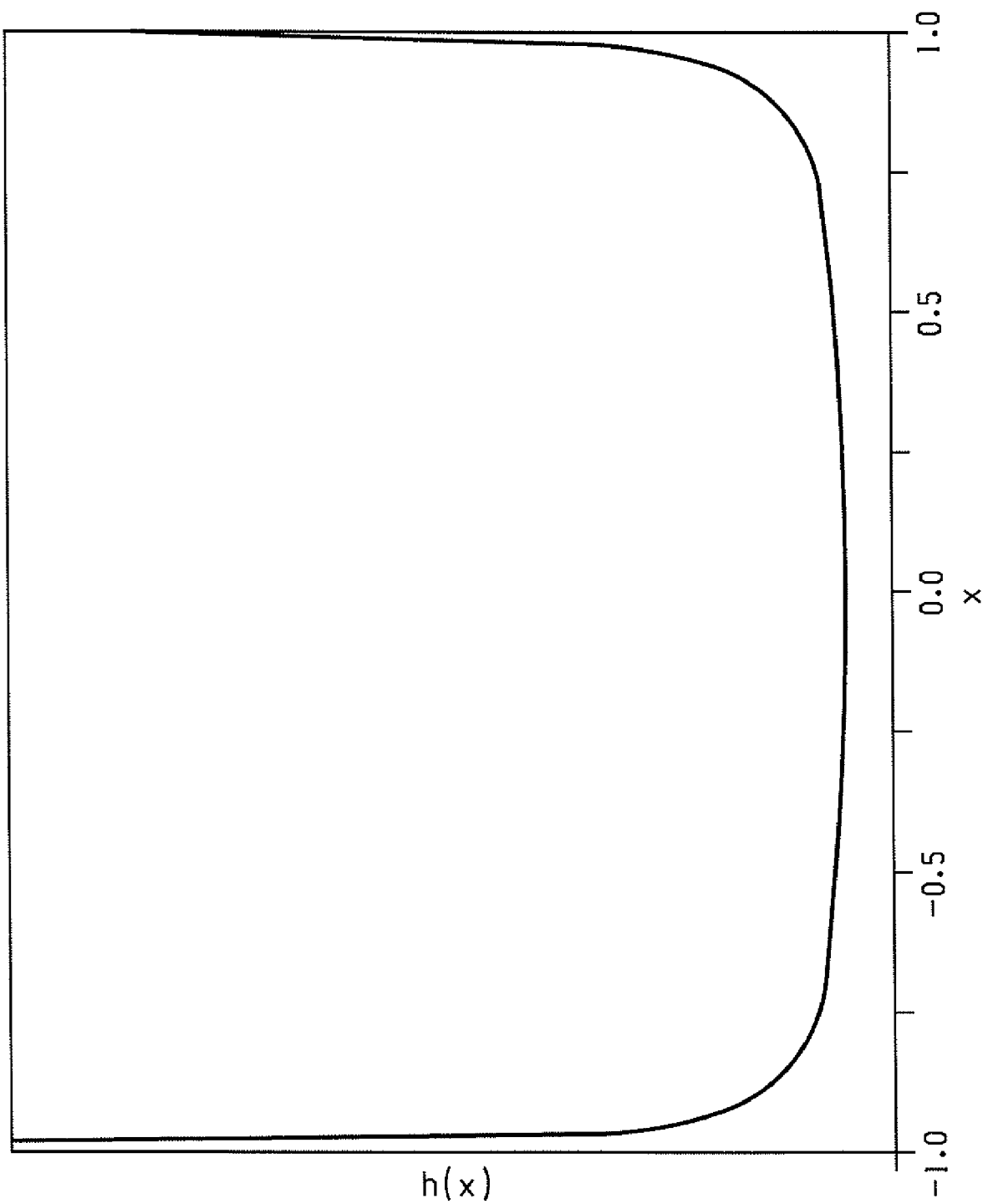
FIG. 8 depicts a spurious coincidence distribution for a highly asymmetric source.

FIG. 6 depicts a slightly asymmetric source $304_s$ located at coordinate (0.1, 0) and a highly asymmetric point source $304_h$ located at coordinate (0.5, 0.5) in the transverse plane of a scanner having a detector ring 302 of radius R=1. FIGS. 7 and 8 depict spurious coincidence distributions for the slightly $304_s$ and highly $304_h$ asymmetric point sources, respectively.

As will be appreciated, the spurious coincidence distributions of FIGS. 7 and 8 are very similar to the analytic expression of Equation 5. Moreover, the shape of the distributions is relatively insensitive to the location of the point source 304, 602, 604. As a consequence, and in the absence of attenuation and scatter, Equation 5 yields a spurious coincidence distribution which approximates that of an extended dirty isotope activity distribution.

Figure 9:
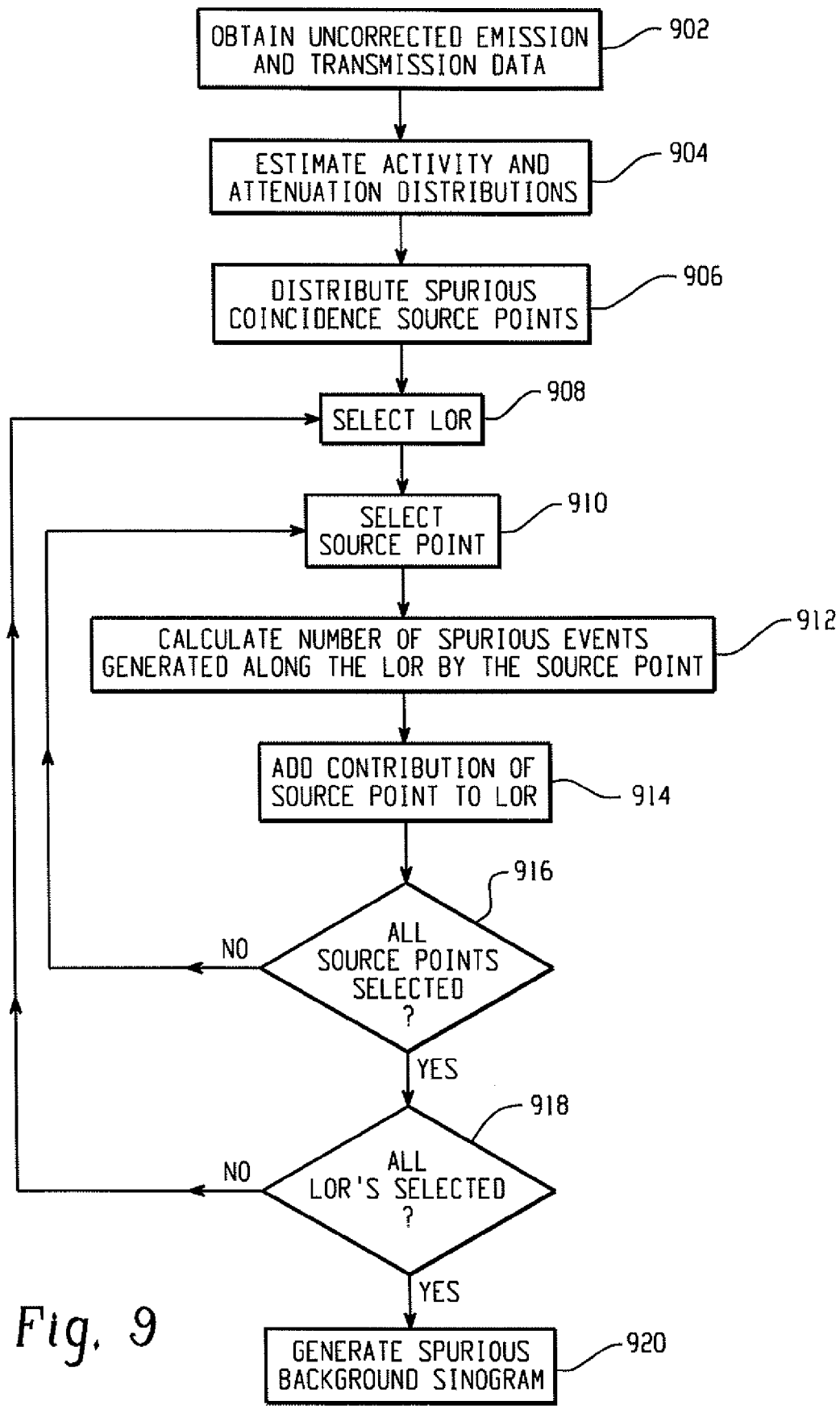
FIG. 9 depicts a technique for generating a spurious coincidence correction.

As activity distribution and physical effects such as attenuation and scatter typically vary from patient to patient and even between successive scans of a particular patient, techniques which account for one or more these factors can be expected to yield even more realistic distributions of spurious coincidences which, when utilized in a correction scheme as described later, lead to a further reduction of the effects of spurious coincidences on image quality. A technique for generating an object specific spurious coincidence correction which addresses such effects is shown in FIG. 9.

At 902, uncorrected emission and transmission data and images are obtained, typically from a scan of the patient or other object under examination.

At 904, uncorrected emission and transmission images are used to estimate the activity distribution of the isotope and attenuation distribution of the object under examination.

At 906, source points for a plurality of spurious coincidence pairs (i.e. one 511 keV annihilation photon and one prompt gamma) are randomly distributed in the attenuation volume. Increasing the number of source points generally increases the accuracy of the correction, whereas reducing the number of source points generally reduces processing time.

At 908, an LOR is selected.

At 910, a source point is selected.

At 912, the activity distribution estimate, solid angles, the attenuation distribution, and the decay scheme of the isotope are used to determine the number of spurious events generated along the LOR by the source point.

At 914, the contribution of the selected source point is added to the selected LOR.

At 916, the process returns to step 910 until all source points have been selected.

At 918, the process returns to step 908 until all LORs have been selected.

At 920, the LOR space is interpolated to obtain a spurious background sinogram.

Note that the correction may also be determined retrospectively. The described correction scheme can be applied once or in an iterative fashion to the uncorrected data. The iterative usage would employ the same steps as illustrated in FIG. 9, but starting from the corrected image data sets of the previous iteration step to estimate the activity and attenuation distribution. The number of iterations can be pre-given by a user or determined from a stopping criterion.

The spurious coincidence correction may be used to reduce the effects of spurious coincidences in the measured projection data. More specifically, corrected projection data $P_{corrected}$ may be generated according to the relationship:

$$P_{corrected} = P_{measured} - a \times S_{Compton} - b \times C - c \times S_{spurious} \qquad \text{Equation 6}$$

where $P_{corrected}$ is the corrected projection data, $P_{measured}$ is the measured projection data, $S_{Compton}$ is a Compton scatter correction preferably implemented using the known SSS technique, CF is a constant or uniform correction factor used to account for errors such as randoms, and $S_{spurious}$ is a correction for spurious coincidences. The spurious coincidence correction $S_{spurious}$ may be advantageously obtained based on the function of Equation 6 or the technique described above in connection with FIG. 9. Scaling factors a, b, and c may be obtained using a best fit technique.

Figure 10:
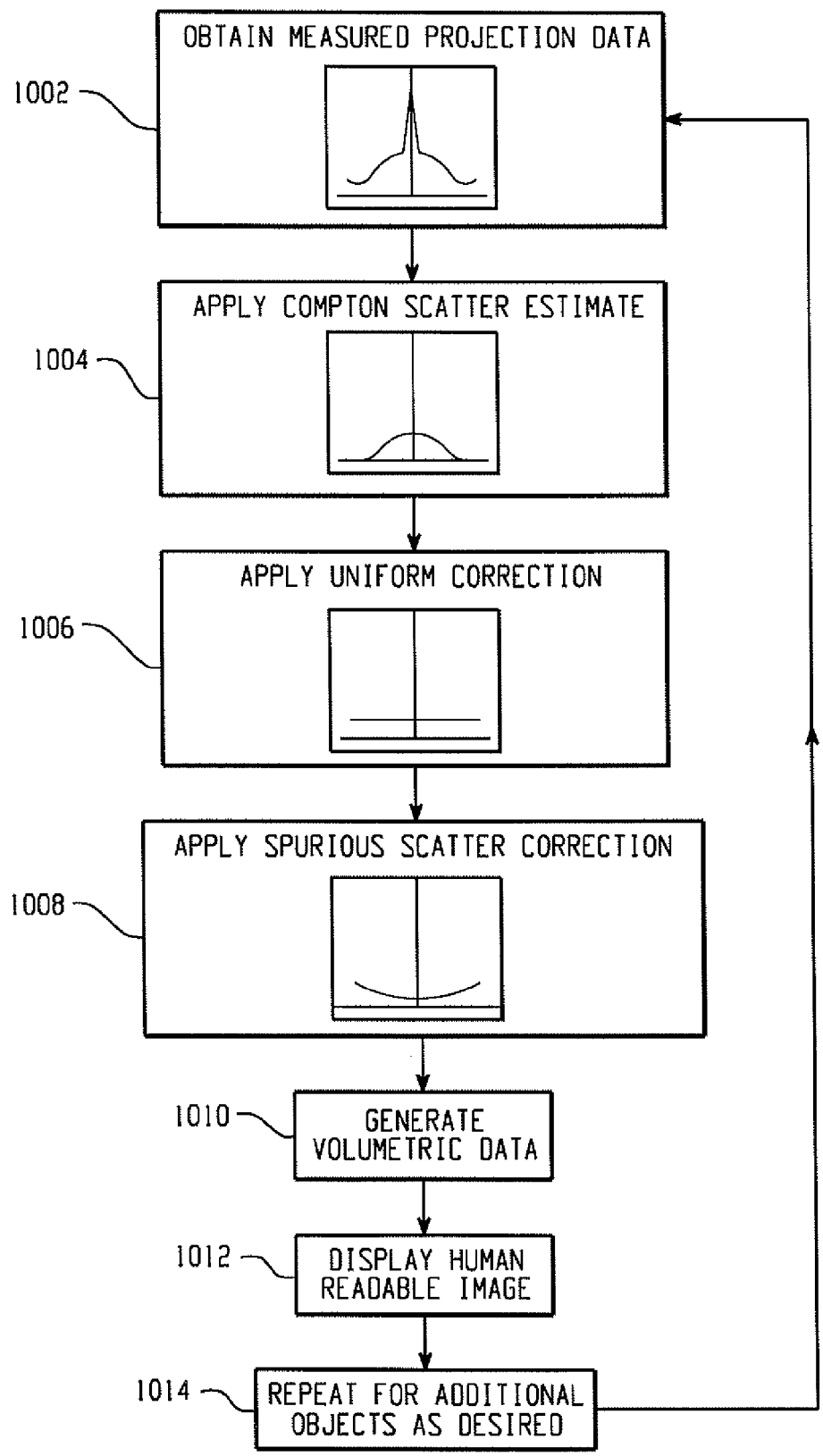
FIG. 10 depicts a technique for correcting position emission data.

The generation of the corrected data $P_{corrected}$ and the reconstruction of volumetric image data indicative of the radionuclide image data will be further illustrated with reference to FIG. 10.

At 1002, a suitable dirty isotope is introduced into the object under examination and PET scanner is used to obtain the measured projection data $P_{measured}$.

At 1004, the Compton scatter correction $S_{Compton}$ is scaled and applied to the measured projection data $P_{measured}$.

At 1006, the uniform correction factor CF is scaled and applied.

At 1008, the spurious scatter correction $S_{spurious}$ is scaled and applied to generate the corrected projection data $P_{corrected}$.

At 1010, the corrected projection data $P_{corrected}$ is reconstructed to generate volumetric data indicative of the distribution of the dirty isotope.

At 1012, the volumetric data is displayed in human readable form, for example on the console 128 or other suitable display, on film, or the like.

In this regard, it should be noted that the corrections 1004, 1006, 1008 may be applied in any desired order. One or more of the corrections may be omitted, others may also be added. Other correction techniques, whether patient specific or otherwise, may be used. Note that the scaling factors a, b, and c may also be obtained in a singe fitting procedure. Some or all of the corrections may also be applied externally to the PET reconstructor 129, for example in the PET data acquisition system 120. It is also expected that suitable attenuation correction would also be applied to correct for attenuation effects in the object under examination.

Of course, modifications and alterations will occur to others upon reading and understanding the preceding description. It is intended that the invention be construed as including all such modifications and alterations insofar as they come within the scope of the appended claims or the equivalents thereof.

What is claimed is:

1. A positron imaging method comprising:
    using information indicative of an attenuation distribution of an object to generate a spurious coincidence correction;
    applying the spurious coincidence correction to data from a positron imaging examination of the object;
    generating a human readable image indicative of the corrected data.

2. The method of claim 1 including using information indicative of an activity distribution in the object to generate the spurious coincidence correction.

3. The method of claim 2 including using data from the positron imaging examination to generate the information indicative of the activity distribution.

4. The method of claim 1 including using data from a CT scan of the object to generate the information indicative of the attenuation distribution.

5. The method of claim 1 wherein using information indicative of an attenuation distribution of the object to generate the spurious coincidence correction includes:
 selecting an LOR;
 selecting a spurious coincidence source location;
 determining a number of spurious events generated along the along the LOR by the source location;
 repeating the step of determining the number of events for each of a plurality of LORs.

6. The method of claim 5 wherein using information indicative of an attenuation distribution of the object to generate the spurious coincidence correction includes repeating the steps of selecting and determining the number of events for each of plurality of source locations.

7. The method of claim 5 including using information indicative of the attenuation distribution to determine the number of events.

8. The method of claim 7 including using information indicative of an activity distribution to determine the number of events.

9. The method of claim 1 including applying at least one of Compton scatter correction and a randoms correction to the data from the positron imaging examination.

10. The method of claim 9 including correcting the data from the positron imaging examination according to the function:

$$P_{corrected} = P_{measured} - a \times S_{Compton} - b \times CF - c \times S_{spurious}$$

where $P_{corrected}$ is the corrected data, $P_{measured}$ is the data from the positron imaging examination, $S_{Compton}$ is the Compton scatter correction, CF is a uniform correction, $S_{spurious}$ is the spurious coincidence correction, and a, b, and c are scaling factors.

11. A positron imaging apparatus comprising:
 means for obtaining data indicative of radionuclide decays in an object under examination, wherein the decays include positron decays which result in the emission of temporally coincident photon pairs and decays which result in the generation of single photons;
 means for measuring a physical characteristic of the object;
 means for using the measured physical characteristic to correct for single photons and single photons of the photon pairs which are detected temporally in coincidence;
 means for generating a human readable image indicative of the corrected data.

12. The apparatus of claim 11 wherein the measured physical characteristic includes a radiation attenuation distribution.

13. The apparatus of claim 11 wherein the measured physical characteristic includes an activity distribution.

14. A computer readable storage medium containing instructions which, when executed by a computer, cause the computer to carry out a method comprising:
 obtaining projection data indicative of positron annihilations in an object under examination, the projection data including spurious coincidences resulting from the decay of a dirty isotope;
 obtaining object specific data indicative of a physical characteristic of the object;
 generating a spurious coincidence correction, which correction is a function of the object specific data;
 using the spurious coincidence correction to correct the projection data;
 generating volumetric image data indicative of the corrected projected data.

15. The computer readable storage medium of claim 14 wherein the spurious coincidence correction is a function of spurious coincidences generated at a plurality of spurious coincidence source locations.

16. The computer readable storage medium of claim 14 wherein the spurious coincidence correction is a function of an object activity distribution.

17. The computer readable storage medium of claim 14 wherein generating the spurious coincidence correction includes:
 determining a number of events generated along an LOR by a spurious coincidence source location;
 repeating the step of determining for a plurality of source locations.

18. The computer readable storage medium of claim 17 wherein the method includes determining a spurious coincidence contribution along each of a plurality of LORs.

19. The computer readable storage medium of claim 14 wherein the physical characteristic includes an attenuation distribution.

20. The computer readable storage medium of claim 14 wherein the step of using the spurious coincidence correction includes applying a scaling factor to the spurious coincidence correction.

21. An imaging method comprising:
 obtaining data indicative of positron annihilations in an object under examination, the data including spurious coincidences;
 applying a spurious coincidence correction to the data so as to reduce an effect of the spurious coincidences, wherein the spurious coincidence correction is a function of an object specific physical characteristic;
 generating a human readable image indicative of the corrected data.

22. The method off claim 21 wherein the object specific physical characteristic includes a spatially varying characteristic.

23. The method of claim 22 wherein the characteristic includes a radiation attenuation.

24. The method of claim 22 including:
 selecting an LOR;
 determining, as a function of the spatially varying characteristic, a number of spurious events generated along the LOR by the source location;
 repeating the steps of selecting and determining for each of a plurality of LORs.

25. The method of claim 21 including using the data to estimate the object specific physical characteristic.

26. A method comprising:
 obtaining measured projection data indicative of positron annihilations in an object under examination;
 using an object specific correction function to correct for Compton scattering and spurious coincidences in the measured projection data;
 generating a human readable image indicative of the corrected projection data.

27. The method of claim 26 including correcting for randoms in the measured projection data.

28. The method of claim 26 wherein the object specific correction function is of the form:

$$P_{corrected} = P_{measured} - a \times S_{Compton} - b \times CF - c \times S_{spurious}$$

where $P_{corrected}$ is the corrected projection data, $P_{measured}$ is the measured projection data, $S_{Compton}$ is a Compton scatter correction, CF is a spatially uniform correction, $S_{spurious}$ is an object specific spurious coincidence correction, and a, b, and c are scaling factors.

29. The method of claim 26 including using data indicative of a characteristic of an interior of the object to correct for the spurious coincidences.

30. The method of claim 29 wherein the data indicative of a characteristic includes x-ray computed tomography data.

31. The method of claim 26 including repeating the steps of obtaining measured projection data, using an object specific correction function, and generating a human readable image for each of a plurality of objects.

32. The method of claim 26 wherein obtaining measured projection data includes obtaining measured projection data acquired using a PET scanner including a ring of radiation sensitive detectors having a radius R and applying a spurious coincidence correction which is proportional to $$\frac{1}{R\sqrt{1-(x/R)^2}},$$

where x is a distance from a center of the ring of radiation sensitive detectors.

33. An apparatus comprising:
a plurality of radiation sensitive detectors disposed about an examination region;
coincidence detection means for generating data indicative of temporally coincident photons detected by the radiation sensitive detectors;
means for correcting for scattering and spurious coincidences in the data according to an object specific correction function so as to generate corrected data;
means for generating a human readable image indicative of the corrected data.

34. The apparatus of claim 33 wherein radiation sensitive detectors are disposed in an arc having a radius R and wherein the means for correcting applies a spurious coincidence correction proportional to $$\frac{1}{R\sqrt{1-(x/R)^2}}$$

where x is a distance from a center of the arc of radiation sensitive detectors.

35. The apparatus of claim 33 wherein the means for correcting applies a spurious coincidence correction which is a function of a radiation attenuation of the object.

36. The apparatus of claim 35 wherein the spurious coincidence correction is a function of an activity in the object.

37. A method of utilizing positron annihilation data acquired using a PET scanner including a ring of radiation sensitive detectors having a radius R, the method comprising:

obtaining data indicative of a plurality of positron annihilations in an object under examination, the data including spurious coincidences resulting from the decay of a dirty isotope;
applying spurious coincidence and attenuation corrections to the data so as to generate corrected data, wherein the spurious coincidence correction is proportional to $$\frac{1}{R\sqrt{1-(x/R)^2}},$$

where x is a distance from a center of the ring of radiation sensitive detectors;
generating a human readable image indicative of the corrected data.

38. The method of claim 37 wherein the corrected data is generated according to the function:

$$P_{corrected} = P_{measured} - a \times S_{Compton} - b \times CF - c \times S_{spurious}$$

where $P_{corrected}$ is the corrected data, $P_{measured}$ is P the data, $S_{Compton}$ is a Compton scatter correction, CF is a uniform correction, $S_{spurious}$ is the spurious coincidence correction, and a, b, and c are scaling factors.

39. A positron imaging apparatus comprising:
a plurality of radiation sensitive detectors disposed about an examination region in an arc having a radius R;
coincidence detection means for generating data indicative of temporally coincident photons detected by the radiation sensitive detectors, the data including spurious coincidences resulting from the decay of a dirty isotope;
means for applying spurious coincidence and attenuation corrections to the data so as to generate corrected data, wherein the spurious coincidence correction is proportional to $$\frac{1}{R\sqrt{1-(x/R)^2}},$$

where x is a distance from a center of the radiation sensitive detector ring;
means for generating a human readable image indicative of the corrected data.

40. The apparatus of claim 39 further including a CT scanner which acquires information indicative of a radiation attenuation of the object.

* * * * *